United States Patent [19]

Black

[11] 4,382,843
[45] May 10, 1983

[54] METHOD FOR PRODUCING GASOLINE-ALCOHOL FUELS

[75] Inventor: Cline Black, Placentia, Calif.

[73] Assignee: Simulation Sciences, Inc., Fullerton, Calif.

[21] Appl. No.: 205,585

[22] Filed: Nov. 7, 1980

Related U.S. Application Data

[63] Continuation-in-part of Ser. No. 126,557, Mar. 3, 1980, abandoned.

[51] Int. Cl.³ .......................... B01D 3/36; B01D 11/04
[52] U.S. Cl. ....................................... 203/19; 203/45; 203/46; 203/69; 203/70; 203/DIG. 13; 568/913

[58] Field of Search .................. 203/18, 19, 39, 43–45, 203/52, 75–77, 79, 82–85, 92, 93, 96–98, DIG. 13; 208/17, 347, 348, 350, 354, 355, 358; 568/913; 44/56

[56] References Cited

U.S. PATENT DOCUMENTS 2,371,010  3/1945  Wolfner ................................ 203/18
2,635,992  4/1953  Carlson et al. ....................... 203/83

*Primary Examiner*—Frank Sever
*Attorney, Agent, or Firm*—Thorpe, North & Western

[57] ABSTRACT

A process for producing gasoline-ethanol blends comprises purifying dilute ethanol by extractive distillation and concentrating the ethanol by distillation followed by one or both of the following steps: (a) liquid extraction of ethanol into heated gasoline or (b) azeotropic distillation of ethanol with an entrainer followed by blending with gasoline.

10 Claims, 3 Drawing Figures

METHOD FOR PRODUCING GASOLINE-ALCOHOL FUELS

BACKGROUND OF THE INVENTION

This application is a continuation-in-part of Ser. No. 126,557, filed Mar. 3, 1980, now abandoned.

This invention relates to a highly flexible process for producing gasoline-alcohol fuel blends such as gasohol, which process provides readily adjustable and positive control of fuel quality at low process energy consumption, producing a fuel suitable for any climatic temperature condition, which fuel, effectively extends scarce petroleum supplies by utilizing ethanol as a component in a gasoline-alcohol fuel blend. The process can utilize ethanol obtained from any source, e.g., ordinary fermentation of biomass, agricultural wastes, forest products, and grains, or from other waste materials, from the hydration of ethylene or from synthesis gas mixtures of carbon monoxide and hydrogen. The gasoline utilized in the process may be obtained from conventional or non-conventional feed stocks.

The addition of alcohols to gasoline to provide fuels for internal combustion engines has often been proposed and sometimes practiced to a limited extent under special circumstances. As the price of gasoline increases, and the supplies from conventional sources become insufficient to meet the demand, the addition of alcohols to gasoline to extend supplies becomes increasingly attractive.

U.S. Pat. No. 4,154,580 teaches the concurrent hydration of olefins in cracked gasolines and the addition of methanol to extend gasoline, and U.S. Pat. No. 3,455,644 teaches the hydration of propylene to form isopropanol for addition to motor fuels. U.S. Pat. No. 4,002,435 teaches the preparation of stable emulsions of gasoline, methanol, and water, with an added component to avoid partial miscibility.

As noted above, methanol has miscibility problems with gasoline, especially at lower temperatures. Isopropanol, while miscible, is costly to produce and is derived primarily from petroleum sources. Ethanol, on the other hand, is the natural product resulting from the fermentation of sugars, starches and cellulose and may also be prepared synthetically.

As the price of fossil-based fuels rises, the use of ethanol as the added component to extend gasoline is becoming economically more attractive. Gasoline-ethanol blends are already being marketed as "gasohol". Ethanol as an extender avoids most of the partial miscibility problems associated with methanol addition and, if produced by fermentation, is a naturally renewable source of energy. However, the crude products from most of the ethanol production methods furnish ethanol in dilute aqueous solution. For example, the ethanol content of most fermentation processes is about 9 to 12 percent by volume. While ethanol is completely miscible with all gasolines, the presence of too much water will cause phase separation. Accordingly, it is desirable to limit the water content of the gasoline-alcohol fuel. Anhydrous, or partially dried, ethanol and gasoline can be then be blended to provide suitable fuels.

Aqueous ethanol can be dried by azeotropic distillation using an entrainer which might be a suitable hydrocarbon, or a mixture of hydrocarbons, suitably prepared heart cut gasoline (HCG), or certain selected oxygenated organic compounds. Benzene has been used, industrially, as the entrainer in the production of dry ethanol. A comparison of benzene with n-pentane and with diethyl either as entrainers for azeotropically drying aqueous ethanol is discussed by Black et.al., in Am. Chem. Soc. Advances In Chemistry Series No. 115, p.64, 1972. The suitability of the entrainers is rated in decreasing order n-pentane, benzene, and diethyl ether. Both U.S. Pat. No. 2,012,199 and U.S. Pat. No. 2,371,010 teach the use of gasoline as an entrainer to azeotropically dehydrate aqueous ethanol. U.S. Pat. No. 3,575,818 teaches the use of pentane as an entrainer. U.S. Pat. No. 2,591,672 teaches the use of gasoline in a, so called, extractive distillation to prepare dry ethanol. Extractive distillation of ethanol using diethylene glycol as solvent has been described and discussed by Black, et.al., Am. Chem. Soc. Advances In Chemistry Series No. 115, p.1, 1972. In addition, Black et.al. show that azeotropic distillation with n-pentane is economically more attractive than extractive distillation with diethylene glycol, for ethanol feeds containing water in slight excess of the azeotropic amount.

While the basic principles and the unit operations of extractive distillation, azeotropic distillation, distillation, and liquid-liquid extraction are well known, the present invention provides a unique combination of these for the purpose of removing water from ethanol and providing a gasoline-ethanol blend which is adaptable for use under any climatic conditions.

BRIEF DESCRIPTION OF THE DRAWINGS

This invention is described with the aid of the accompanying general process flow diagrams which depict three different modes of operation.

SUMMARY OF THE INVENTION

Figure 1:
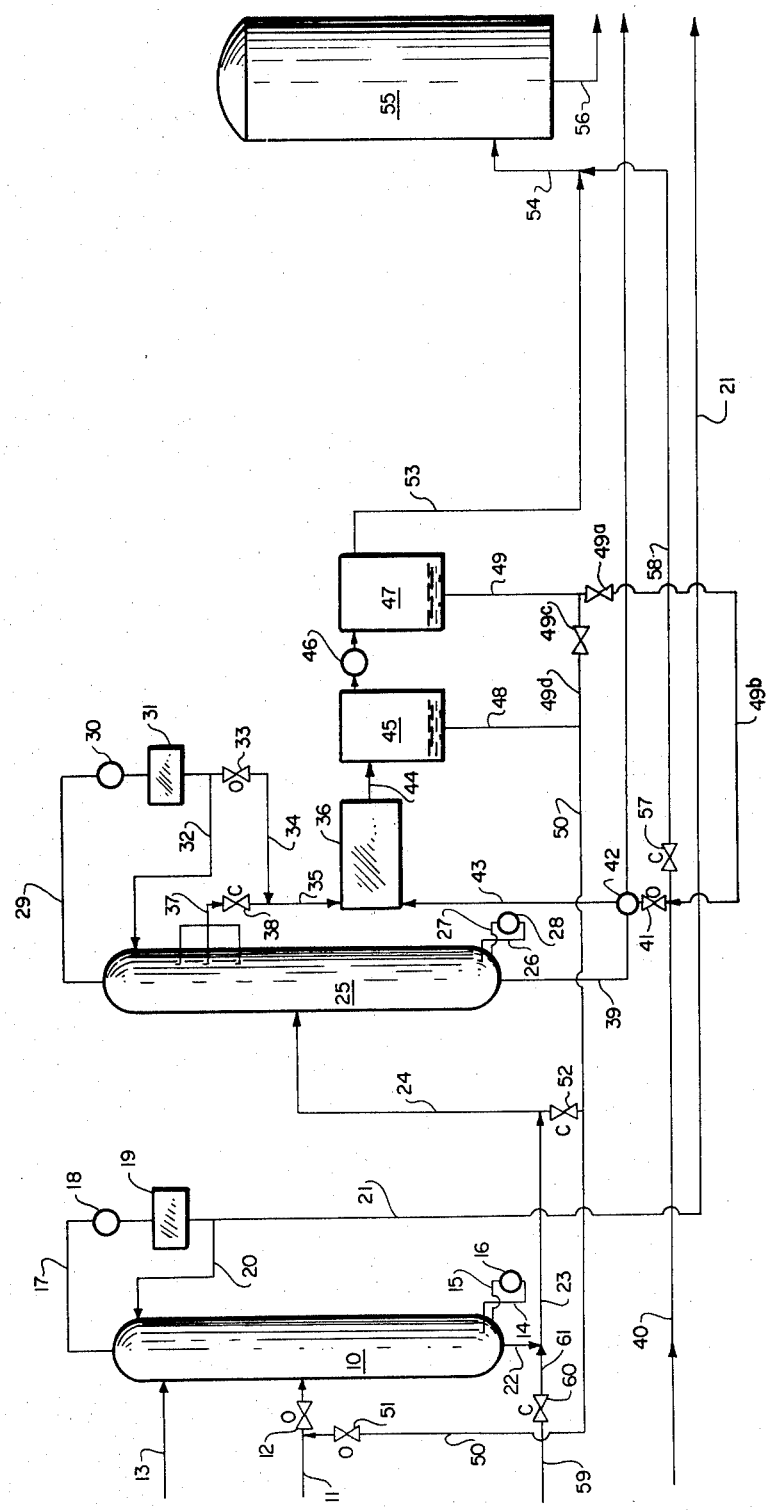
FIG. 1 illustrates a schematic flow diagram for providing gasoline-ethanol blends utilizing a three-step process of extractive distillation, distillation and liquid extraction.

In the first mode of operation, illustrated in FIG. 1, high molecular weight impurities are removed from the ethanol feed stream by extractive distillation with water as solvent. The purified dilute ethanol stream is concentrated by distillation to give a top product rich in ethanol and a bottom which is water. The top product contains 45 to 80 percent mole ethanol and is mixed with gasoline to produce a mixture which is phase separated at high temperature to give a gasoline phase rich with ethanol and some dissolved water and an aqueous phase containing some ethanol. The ethanol-enriched gasoline phase is cooled to give a mixture which is phase separated at low temperature to produce a gasoline-ethanol blend and a small aqueous phase containing some ethanol which may be recycled back to the extractive distillation zone, to the feed to the ethanol concentrator, or to the gasoline feed which is then heated before entering the mixer.

Figure 2:
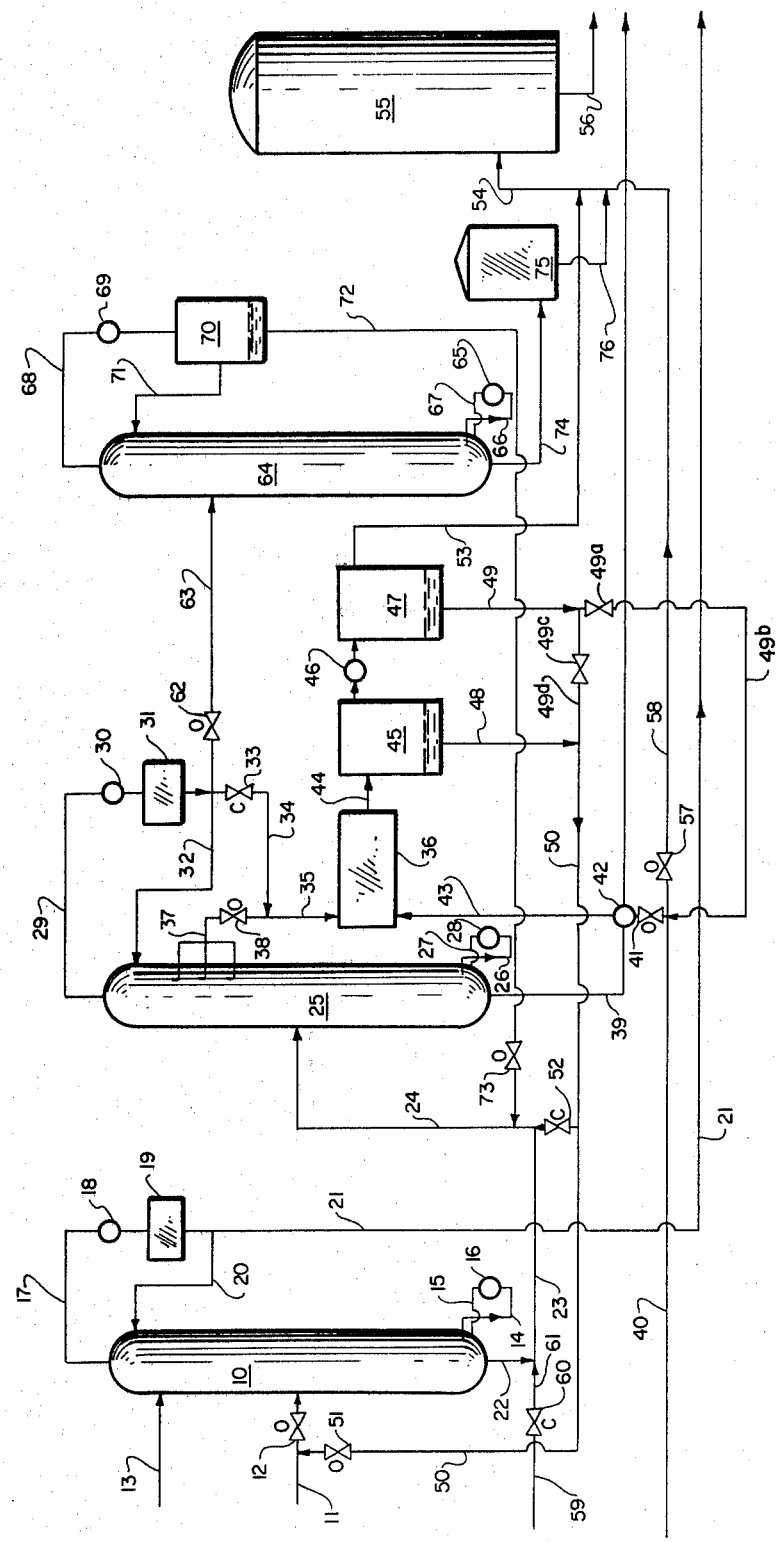
FIG. 2 illustrates a process similar to FIG. 1 in which an azeotropic distillation step has been added.

In the second mode of operation, illustrated in FIG. 2, the extractive distillation column is operated as described to reject impurities and to produce an ethanol stream from an azeotropic distillation column to provide a feed to the second distillation column. This column produces a near-azeotropic ethanol-water mixture, i.e., 75 to 89 percent mole ethanol as top product and a side cut product containing 45 to 70 percent mole ethanol. The side cut is mixed with gasoline, phase separated at high temperature, and the gasoline phase is cooled, phase separated a second time at low temperature to produce a gasoline-ethanol blend and a small aqueous phase as described in the first mode of operation. The near azeotropic ethanol-water mixture from the second distillation column provides the feed to the azeotropic distillation column using an entrainer, such as a heart cut gasoline or n-pentane, to produce dry ethanol as a bottom product and an aqueous phase as a top product which is recycled and combined with the feed to the second distillation column. The dry ethanol may be stored and later mixed with gasoline to produce a final mixed gasoline-ethanol blend, i.e., gasohol.

In the third mode of operation, the gasoline liquid extraction step is bypassed. In this mode, the extractive distillation column removes, as in the other two modes of operation, the high boiling impurities as top product. The bottom aqueous ethanol product is combined, as in the second mode, with the recycle stream from the azeotropic distillation column to make the feed to the second distillation column. In this mode of operation, all ethanol fed to the second distillation column is removed as a near azeotropic mixture of ethanol-water as top product and excess water is removed as the bottom product. The ethanol-water mixture is azeotropically distilled using an entrainer to produce dry ethanol as a bottom product and an aqueous top stream, which is recycled. The dry ethanol is stored and later mixed with gasoline in desired proportions to produce gasohol.

For high quality ethanol feeds, which contain no odor producing, or otherwise objectionable high molecular weight components, the extractive distillation step can be bypassed or eliminated with the feed stream entering directly into the second distillation column.

By suitable adjustment of the valves, either type of feed can be processed separately or both types can be processed simultaneously.

DETAILED DESCRIPTION OF THE INVENTION

The present invention is a highly flexible process for producing gasoline-alcohol fuels, e.g., gasohol, which process provides readily adjustable and positive control of fuel quality at low process energy consumption, producing a fuel suitable to any climatic temperature condition, which fuel effectively extends scarce petroleum supplies by utilizing ethanol as an added component in a gasoline-alcohol fuel blend.

The process consists of an aqueous extractive distillation step to provide odor and quality control, an ordinary distillation step to concentrate dilute aqueous ethanol mixtures, a single stage liquid-liquid extraction step to transfer ethanol from a suitably prepared aqueous ethanol mixture to a gasoline phase, a cooler and settler stage to further reduce water, and an azeotropic distillation stage to dehydrate near azeotropic mixtures of ethanol and water which provides high quality dry ethanol for fuel blending or for other uses. Depending upon the purity of the aqueous ethanol feedstock, the extractive distillation step may or may not be required. Hence, this step becomes an integral part of the invention only when needed.

FIG. 1 illustrates one embodiment of the invention comprising an extractive distillation step, a conventional distillation step and a single stage liquid extraction step.

When operating according to this embodiment an ethanol feedstock, such as obtained from a fermentation process, enters extractive distillation column 10 via line 11 through open valve 12. Water as a solvent enters the upper portion of column 10 through line 13. Heat is supplied to column 10 by means of liquid from the column being reboiled and circulated via lines 14 and 15 through heater 16. Ethanol vapors are extracted from the vapor phase by water entering the top of the column and high molecular weight impurities exit the top of column 10 through line 17 where they are condensed in condenser 18 and collected in chamber 19. These condensed impurities may contain some ethanol and some may reenter column 10 as a reflux stream through line 20 while the remainer is drained from the system via line 21. The purified dilute ethanol in the bottom of column 10 is drawn via lines 22, 23 and 24 into a second distillation column 25 where the ethanol is concentrated.

The water-ethanol mixture is heated in column 25 by means of liquid from the column being passed through lines 26 and 27 through heater 28. The top product exiting line 29 is condensed in condenser 30 and collected in chamber 31. This product contains 45 to 70 percent mole ethanol, part of which may be recycled as a reflux back to column 25 via line 32 while the top product passes via open valve 33 through lines 34 and 35 into mixer 36. Provision is also made to draw a side cut portion from column 25 via line 37 and valve 38 to the mixing tank 36. However, in this embodiment, valve 38 is preferably closed. Hot water from column 25 is drawn from the system through line 39.

Gasoline enters the system via line 40 through open valve 41 and is heated in heat exchanger 42 by the hot water exiting column 25. The heated gasoline passes through line 43 into mixer 36 where it is mixed with the condensed concentrated ethanol. The gasoline-ethanol-water mixture passes via line 44 into tank 45 for phase separation. Under the conditions described herein, the ethanol is distributed at the concentration desired into the gasoline phase. This upper gasoline phase is thus enriched with ethanol and the lower aqueous phase becomes ethanol lean or depleted. The gasoline-ethanol blend is withdrawn from tank 45 into cooler 46 and passed into tank 47 for further phase separation at low temperature into a purified gasoline-ethanol blend, suitable for use as a fuel in internal combustion engines, and a small aqueous phase. The temperature at which the last phase separation is carried out will depend upon the climatic conditions under which the gasoline-alcohol blend is to be used. For example, if the phase separation is carried out at 0° C., the blend can be used under climatic conditions as low as that temperature without there being any phase separation of water from the blend. Obviously, the separation step may be adjusted to higher or lower temperatures as required. The aqueous phases from tanks 45 and 47 are withdrawn via lines 48 and 49 into line 50, when valve 49-c and line 49-d are open, for recycle through valve 51 to column 10 or through valve 52 to column 25, depending on the quality of the ethanol feed. Alternatively, the second lower aqueous phase from line 49 may pass through open valve 49-a, through 49-b, to join line 40.

The gasoline-ethanol blend in tank 47 is withdrawn via lines 53 and 54 into storage tank 55 from which it may be withdrawn from the system for use as a fuel via line 56. In some instances, the ethanol content in line 53 may be higher than desired for certain climatic conditions in which case valve 57 may be opened and the desired amount of gasoline may be metered into line 58 to dilute the ethanol content of the blend entering storage tank 55.

Should a sufficiently pure source of aqueous ethanol be available, the extractive distillation step may be omitted and the aqueous ethanol may be fed to column 25 through line 59, valve 60, line 61, line 23, and line 24.

FIG. 2 illustrates the preferred embodiment of the invention and functions essentially as described in FIG. 1 with the addition of an azeotropic distillation step. The numbering on FIG. 2 remains the same as in FIG. 1 except for the added step. Hence, only the additional functioning of the azeotropic distillation step will be described. In this embodiment, the purified dilute ethanol entering column 25 is distilled under more exacting conditions to produce a top product exiting line 29 which is a near azeotropic ethanol-water mixture, i.e., 75 to 89 percent m ethanol, and a side product containing 45 to 70% m ethanol is withdrawn from upper trays within column 25 via line 37 and open valve 38 into line 35 and thence to mixer 36. This side cut product has essentially the same ethanol concentration as obtained as a top product in FIG. 1 and is processed by liquid gasoline extraction in the same manner as already described.

The near-azeotropic top product from column 25 is condensed in condenser 31 and then passed through open valve 62 and line 63 into azeotropic distillation column 64 where it is azeotropically distilled using an entrainer to produce dry ethanol as a bottom product and water with entrainer and some ethanol as a top product.

The entrainer used is preferably n-pentane or a heart cut gasoline (HCG) which has been fractionated to remove any and all aromatic components and most other components boiling above n-hexane as a heavy boiling fraction and to remove the most volatile components, propane, butane and isobutane as a light boiling fraction. Typical of components which might be included in HCG are isopentane, pentane, cyclopentane, 2,2-dimethylbutane, 2,3-dimethylbutane, 2-methylpentane, 3-methylpentane and n-hexane.

The column 64 is heated by liquid which is reboiled and circulated through heater 65 via lines 66 and 67. The water and entrainer exiting the top of column 64 through line 68 is liquified in condenser 69 and collected in chamber 70 where it phase separates into a top entrainer product and a bottom dilute aqueous ethanol product. The entrainer in chamber 70 is recycled as a reflux through line 71 to the top portion of column 64 and the aqueous ethanol is recycled via line 72 through open valve 73 to mix with dilute ethanol in line 24 and returned to column 25 for reconcentration.

The bottom product withdrawn from column 64 via line 74 into storage tank 75 is dry ethanol. This product may be withdrawn from tank 75 through line 76 and blended with gasoline from line 58 in line 54 to form the desired gasohol blend in tank 55. Gasohol from tank 47 may also be metered into line 54 as desired. Thus dry ethanol from tank 75, gasoline-ethanol blends which have been cooled to low temperatures from tank 47 and gasoline may be blended in any desired proportions to formulate a gasohol fuel having the desired ethanol content. Moreover, process conditions may be changed to formulate a gasohol fuel suitable for the climate in which the fuel is to be used.

Figure 3:
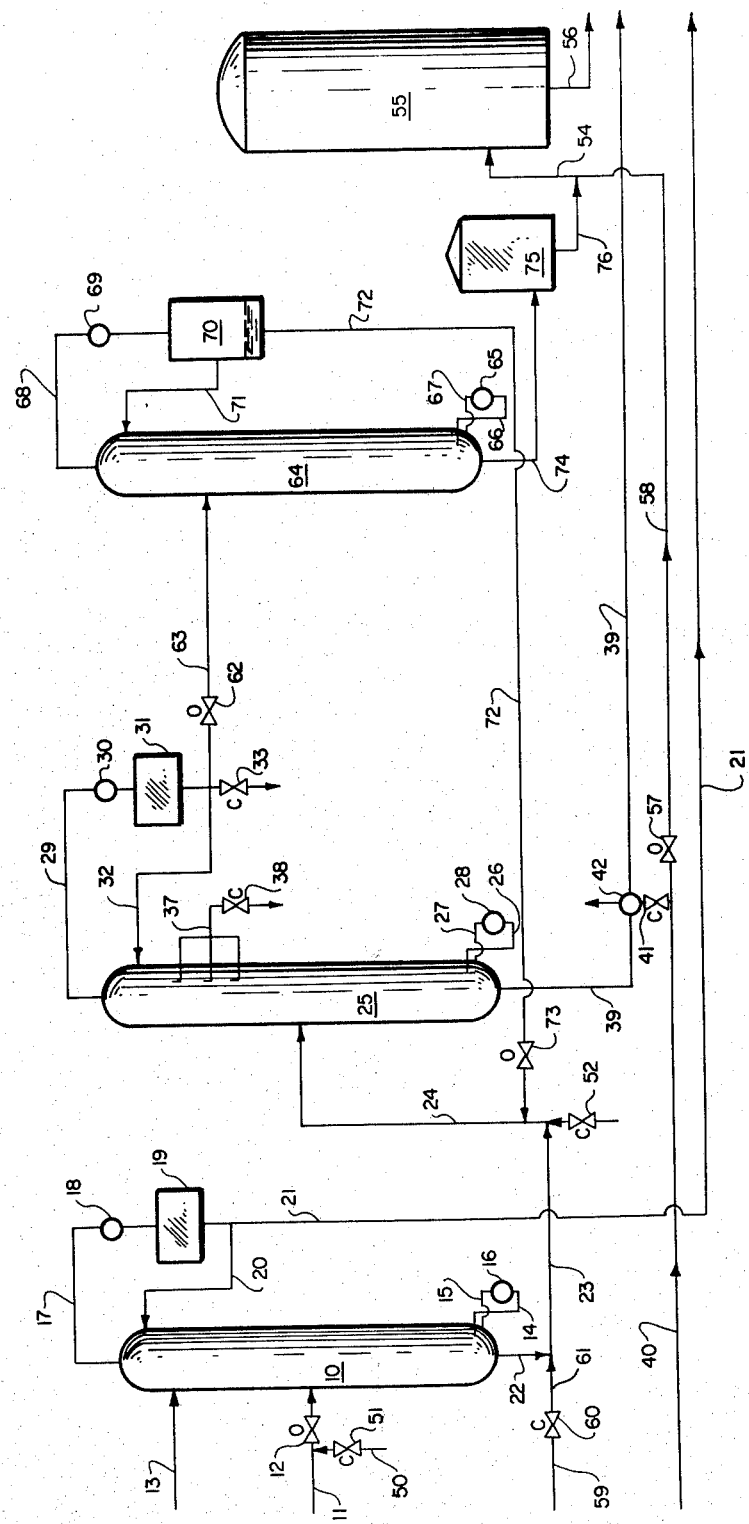
FIG. 3 illustrates a process similar to FIG. 2 wherein the liquid extraction step has been omitted.

The third mode of preparing a gasoline-ethanol blend is shown in FIG. 3 and differs from the method described in FIG. 2 in that the liquid-liquid extraction step involving mixer 36, phase separation tank 45 and 47 and cooler 46, has been removed.

In this mode all ethanol from column 25 is removed as a near-azeotropic mixture via line 29 and no side cut is taken. All excess water is removed via line 39. The near-azeotropic mixture is azeotropically distilled in column 64 with an n-pentane or HCG entrainer as previously described to produce a dry ethanol which is stored in tank 75. The dry ethanol is then blended with gasoline to produce a gasohol blend as desired.

While the above description details three basic modes of operation, it is to be realized that various combinations are possible. For example, valve 60 can be opened and ethanol feedstocks from both lines 59 and 22 may simultaneously be fed to column 25. Also the distillation column 25 can be utilized to fractionate gasoline to prepare HCG as an entrainer. The more volatile components are removed overhead and the higher boiling product is removed as a bottom product with HGC being removed as a side cut via line 37.

As previously mentioned, the process can be operated with both low and high quality feeds, either processing each separately, or both simultaneously. Low quality feeds entering via line 11 and valve 12 are those which contain odor producing or otherwise objectionable high molecular weight components, i.e., butyraldehyde valeraldehyde and crotonaldehyde. While some of the high molecular weight components are not objectionable, they are also removed in the top product from the aqueous extractive distillation column 10. High quality feeds, entering via line 59 and valve 60, bypass the extractive distillation column 10 and flow directly, when combined with recycle from open valve 52, to the ethanol concentrator column 25. These feeds contain no odor forming, or otherwise objectionable high molecular weight components which must be removed.

The most general mode of operating the process is Mode 2 operating with either single feeds, or simultaneously with both, as described in FIG. 2. When operating in this way, dry ethanol of high quality is produced and is available for fuel blending and for other uses. This provides a second and final control on the composition and quality of the gasohol which can be tailored to meet any climatic temperature condition, avoiding the problem of water phase separation. In addition, if feed ethanol in excess of that required for fuel blending is available, high quality ethanol can be produced for other purposes. If the preferred entrainers, HCG or n-pentane, are used for azeotropically drying the ethanol, no traces of objectionable aromatic compounds will appear in the ethanol product.

If dry ethanol is not required, the process can be operated according to Mode 1, FIG. 1, where the azeotropic distillation column has been bypassed or eliminated from the process flow. Either single feeds or double feeds can be processed. Where only a high quality ethanol feed from line 59 is used, the extractive distillation column can also be bypassed or eliminated, and the operation becomes the simplest and the most economical of all.

On the other hand, if dry ethanol of high quality is the main objective and fuel blending is only a minor objective, the process can be operated according to Mode 3, FIG. 3, by bypassing the single stage solvent extraction step. If a preferred entrainer, HCG or n-pentane, is used in the azeotropic distillation step, no traces of objectionable aromatic impurities will appear in the dried ethanol.

The single stage liquid-liquid extraction step, used when operating according to Modes 1 and 2, is carried out at high temperature, 60° to 110° C., since the distribution coefficient for ethanol, while more favorable to the water phase at low temperatures, becomes progressively less favorable to the water phase and progressively more favorable to the gasoline phase as the temperature is raised. Accordingly the concentration of ethanol in the recycled aqueous phase through line 48 becomes progressively lower as the extraction temperature is raised. In certain preferred operations, it goes through a minimum value. Temperatures above 110° C. can be used but are not usually needed. Heat exchange between the hot water stream from column 25 and the gasoline stream in heat exchanger 42 preheats the gasoline, in line 43, before it is mixed with aqueous ethanol from line 35 in mixer 36 for the single stage extraction at high temperature and phase separated in tank 45.

Process conditions such as temperatures, pressures, flow rates and the like may be determined on a case-by-case basis and may be determined by one having ordinary skill in the art.

The following examples illustrate various operative embodiments of the invention but are not to be considered as limitations of the invention.

In each of the following examples, the same quantity of a low quality ethanol feed, such as is obtained from the hydration of ethylene, is processed to recover the same amount of ethanol in a blended gasoline-ethanol mixture having an ethanol concentration of 10 percent mole. A complete material balance is given in each example based on an ethanol recovery of about 99 percent from the feed. Any ethanol losses are in the top product from the extractive distillation column. Otherwise, complete recovery of the ethanol is achieved. All quantities throughout each example are based on pound moles of components per hour.

EXAMPLE 1

The process described in FIG. 1 is utilized in this example. Flows are in lb-moles per hour.

A feed as shown in Table 1a is fed into extractive distillation column 10.

TABLE 1a

| Feed Components | Crude Feed (Line 11) | Recycle (Lines 48,49,50) | Fresh Water |
|---|---|---|---|
| Gasoline | 0 | 0.125 | 0 |
| Impurities* | 21.0 | 0.00 | 0 |
| Ethanol | 218.877 | 29.60 | 0 |
| Water | 1,770.914 | 174.60 | 958.022 |
| Total | 2,010.791 | 204.325 | 958.022 |

*High molecular weight alcohols, aldehydes, ketones, ethers, etc.

The process conditions within the extractive distillation column 10 are such that the impurities are taken off as a top product, which is condensed and disposed of, and a purified dilute ethanol is taken as bottom product. The composition of these products is shown in Table 1b.

TABLE 1b

| Components From Extractive Distillation | Top Product (Lines 17,21) | Bottom Product (Lines 22,23,24) |
|---|---|---|
| Impurities | 21.0 | (Trace) |
| Ethanol | 2.24 | 246.237 |

TABLE 1b-continued

| Components From Extractive Distillation | Top Product (Lines 17,21) | Bottom Product (Lines 22,23,24) |
|---|---|---|
| Water | 61.00 | 2,842.536 |
| Total | 84.24 | 3,088.773 |

The bottoms, purified ethanol, from Column 10 is passed into distillation column 25 wherein the ethanol is distilled and recovered as a top product in concentrated form and heated water is removed as a bottom product which, after being used for heating gasoline, is removed from the system. The material balance of products from distillation Column 25 are shown in Table 1c.

TABLE 1c

| Components From Distillation Column | Top Product (Lines 29,34,35) | Bottom Product (Line 39) |
|---|---|---|
| Ethanol | 246.237 | 0 |
| Water | 182.100 | 2660.436 |
| Total | 428.337 | 2660.436 |

The condensed concentrated ethanol from line 35 passes into mixer 36 where it is mixed with gasoline from line 43 which has been heated in heat exchanger 42 by the hot water exiting column 25 via line 39. The gasoline is fed into mixer 36 at the rate of 1,943.989 lb. moles/hr. The combined gasoline-ethanol mixture has a temperature of 81.5° C. and passes via line 44 into separation tank 45 where it is separated into a top gasoline ethanol phase and a lower first aqueous phase. The gasoline-ethanol phase is cooled to 0° C. in cooler 46 and passed to tank 47 and the aqueous phase is withdrawn via line 48. The composition of these phases is shown in Table 1d.

TABLE 1d

| Phase Components | Gasoline Phase | First Aqueous Phase |
|---|---|---|
| Gasoline | 1,943.880 | 0.109 |
| Ethanol | 221.342 | 24.895 |
| Water | 29.283 | 152.817 |
| Total | 2,194.505 | 177.821 |

The gasoline-ethanol phase in tank 47 separates at 0° C. into a gasohol phase and a second aqueous phase. The gasohol is withdrawn via lines 53 and 54 to storage tank 55 for use as a fuel, and the second aqueous phase is withdrawn via line 49 to be combined with the first aqueous phase for recycle to column 10. The composition of the gasohol and second aqueous phases is shown in Table 1e.

TABLE 1e

| Phase Components | Gasohol Blend | Second Aqueous Phase |
|---|---|---|
| Gasoline | 1,943.864 | 0.016 |
| Ethanol | 216.637 | 4.705 |
| Water | 7.500 | 21.783 |
| Total | 2,168.001 | 26.504 |

The gasohol product produced according to this example can be used at any climatic temperature, 0° C. and higher, without encountering any difficulty due to phase separation of water. By lowering the temperature of product passing through cooler 46 to the minimum climatic temperature at which the fuel is to be used, difficulty due to phase separation will always be avoided. Obviously the cooler the temperature of the gasohol blend in separation tank 47 the lower the amount of water retained in the blend will be.

The ethanol concentration in the final gasohol blend may be varied as desired by modifying the operation of the ethanol concentrator, column 25, the gasoline-ethanol mixer 36 and separation tank 45. For example, the ethanol concentration from column 25 may be varied by changing operation conditions, and the exchange of ethanol into the gasoline phase may be modified by temperature adjustment.

EXAMPLE 2

The process described in FIG. 2 is used in this example. All flows are given in lb-moles per hour.

A feed as shown in Table 2a is fed into extractive distillation column 10.

TABLE 2a

| Feed Components | Crude Feed (Line 11) | Recycle (Lines 48,49,50) | Water (Line 13) |
|---|---|---|---|
| Gasoline | 0 | 0.081 | 0 |
| Impurities* | 21.0 | 0 | 0 |
| Ethanol | 218.877 | 19.543 | 0 |
| Water | 1,770.914 | 113.213 | 903.3154 |
| Total | 2,010.791 | 132.837 | 903.3154 |

*High molecular weight alcohols, aldehydes, ketones, ethers, etc.

The process conditions within extractive distillation column 10 are such that the overhead product contains essentially all of the impurities along with 2.24 lb. moles/hr. of ethanol and 61.0 lb moles/hr. of water. The bottom product, consisting of purified dilute ethanol along with recycled aqueous ethanol from the operation of azeotropic distillation column 64 are fed to distillation column 25 for ethanol concentration. This feedstock has the composition shown in Table 2b.

TABLE 2b

| Composition Components (Line 24) | Bottoms From Column 10 (Lines 22,23) | Recycle From Column 64 (Line 72) | Total Feed (Line 24) |
|---|---|---|---|
| Entrainer* | 0 | 0.160 | 0.160 |
| Ethanol | 236.180 | 5.580 | 241.760 |
| Water | 2,726.4424 | 16.5576 | 2,743.000 |
| Total | 2,962.6224 | 22.2976 | 2,984.9200 |

*HCG or n-pentane

The feed from Table 2b is distilled in Column 25 to provide three streams, a concentrated ethanol product removed via line 29, a side draw ethanol product withdrawn through line 37 and heated water withdrawn through line 39 and disposed of after heat exchange in exchanger 42. The composition of the three streams from column 25 is given in Table 2c.

TABLE 2c

| Composition Components | Top (Line 63) | Side Draw (Line 37) | Bottom (Line 39) |
|---|---|---|---|
| Entrainer | 0.1597 | 0.0003 | 0 |
| Ethanol | 81.84 | 159.92 | 0.0001 |
| Water | 16.56 | 118.23 | 2,608.21 |
| Total | 98.560 | 278.1503 | 2,608.21 |

The overhead product from line 29 is condensed in condenser 30, collected in chamber 31 and passed through line 63 to azeotropic distillation column 64 where the water is azeotropically distilled from the ethanol using an entrainer which is either HCG or n-pentane. The water-entrainer-ethanol mixture is removed overhead via line 68, condensed in condenser 69 and collected in container 70 where it is phase separated. The upper entrainer phase is recycled via line 71 back to column 64 and the aqueous ethanol phase is recycled to column 25. Dry ethanol is removed as a bottom product from column 64 and stored in tank 75. The composition of the aqueous recycle to column 25 is given in Table 2b. The entrainer recycle and the dry ethanol product is given in Table 2d.

TABLE 2d

| Composition Components | Entrainer Recycle (Line 71) | Dry Ethanol (Line 74) |
|---|---|---|
| Entrainer | 245.51 | 0 |
| Ethanol | 28.00 | 76.26 |
| Water | 2.46 | 0.0024 |
| Total | 275.97 | 76.2624 |

The side draw ethanol from line 37 is drawn via line 35 into mixer 36 where it is mixed with gasoline from line 43 which has been heated in heat exchanger 42 by hot water in line 39. The gasoline diverted from line 40 via exchanger 42 is fed to mixer 36 at the rate of 1,109.0 lb. mole/hr. The combined gasoline-ethanol mixture formed in mixer 36 has a temperature of 81.5° C. and passes into separation tank 45 where it is phase separated into an upper gasoline-ethanol phase and a lower dilute ethanol first aqueous phase. The gasoline-ethanol phase is withdrawn to cooler 46 where it is cooled to 0° C. and passed to tank 47, and the aqueous phase is withdrawn via line 48 for recycle. The compositions of the gasoline-ethanol phase and the aqueous ethanol phase from tank 45 are given in Table 2e.

TABLE 2e

| Composition (Tank 45) | Gasoline Phase (To Cooler 46) | First Aqueous Phase (Line 48) |
|---|---|---|
| Gasoline | 1,108.930 | 0.070 |
| Ethanol | 143.752 | 16.168 |
| Water | 20.369 | 97.861 |
| Total | 1,273.051 | 114.099 |

The gasoline-ethanol phase in tank 47 separates at 0° C. into a gasoline-ethanol blend and a second aqueous phase. The gasoline-ethanol blend is withdrawn via line 53 for blending in line 54 with gasoline and/or ethanol, and the second aqueous phase is withdrawn via line 49 to be combined with the first aqueous phase for recycle to column 10. The composition of products from Tank 47 is given is Table 2f.

TABLE 2f

| Composition Components | Gasoline-Ethanol Phase (Line 53) | Second Aqueous Phase (Line 49) |
|---|---|---|
| Gasoline | 1,108.919 | 0.011 |
| Ethanol | 140.377 | 3.375 |
| Water | 5.017 | 15.352 |
| Total | 1,254.313 | 18.738 |

A completed gasohol product is formulated by blending together the gasoline-ethanol phase from line 53 and the dry ethanol from lines 74 and 76 at the rates in which they are prepared along with an additional 840.814 lb. mole/hr. of gasoline fed via line 58 into line 54. The completed gasohol in tank 55 thus has the composition shown in Table 2g.

TABLE 2g

| Composition Components | Gasoline (Line 58) | Gasoline-Ethanol (Line 53) | Dry Ethanol (Line 74,76) | Total (Line 54) |
|---|---|---|---|---|
| Gasoline | 840.814 | 1,108.919 | 0 | 1,949.733 |
| Ethanol | 0 | 140.377 | 76.26 | 216.637 |
| Water | 0 | 5.017 | 0.0024 | 5.0194 |
| Total | 840.814 | 1,254.313 | 76.2624 | 2,171.3894 |

As in Example 1, the gasohol product could be adapted for other climates by changing the temperature of cooler 46. Also the amount of water can be controlled as in Example 1 with an additional variable side draw 37. The location of side draw 37 on column 25 may be varied according to the ethanol concentration desired.

Moreover, in this example the final composition of the gasohol may be more widely varied by storing the dry ethanol in tank 75 and metering it through line 76 in desired proportions. Also the rate at which gasoline is fed through line 58 may be varied as desired. Hence, compositions containing any desired gasoline to ethanol ratio may be prepared and the amount of water in such compositions may be predetermined to produce a gasohol for any climate.

EXAMPLE 3

The process described in FIG. 3 is used in this example.

The feedstock shown in Table 3a is fed to extractive distillation column 10. All flows are in lb-moles per hour.

TABLE 3a

| Feed Components | Crude Feed (Line 11) | Water (Line 13) |
|---|---|---|
| Impurities* | 21.000 | 0 |
| Ethanol | 218.877 | 0 |
| Water | 1,770.914 | 970.854 |
| Total | 2,010.791 | 970.854 |

*High molecular weight alcohols, aldehydes, ketones, ethers, etc.

The process conditions within extractive distillation Column 10 are such that the overhead product contains essentially all of the impurities along with 2.24 lb moles/hr. of ethanol and 61.0 lb. moles/hr. of water. The bottom product, consisting of purified dilute ethanol along with recycled aqueous ethanol from the operation of azeotropic distillation column 64 are fed to distillation column 25 for ethanol concentration. This feedstock has the composition shown in Table 3b.

TABLE 3b

| Composition Components | Bottoms From Column 10 (Line 22) | Recycle From Column 64 (Line 72) | Total Feed To Column 25 (Line 24) |
|---|---|---|---|
| Entrainer* | 0 | 0.466 | 0.466 |
| Ethanol | 216.637 | 16.111 | 232.748 |
| Water | 2,500.768 | 48.295 | 2,549.063 |
| Total | 2,717.405 | 64.872 | 2,782.277 |

*HCG or n-pentane

The feed from Table 3b is distilled in Column 25 to provide a concentrated ethanol top product removed via line 29 and a bottom heated water product withdrawn via line 39 and used as a source of heat for heat exchanger 42. No side draw is taken as in Example 2. The composition of products removed from column 25 is shown in Table 3c.

TABLE 3c

| Composition Components | Top (Line 63) | Bottom (Line 39) |
|---|---|---|
| Entrainer | 0.466 | 0 |
| Ethanol | 232.748 | 0 |
| Water | 47.560 | 2,501.503 |
| Total | 280.774 | 2,501.503 |

The overhead product from line 29 is condensed in condenser 30, collected in chamber 31 and passed through line 63 to azeotropic distillation column 64 where the water is azeotropically distilled from the ethanol using an entrainer which is either HCG or n-pentane. The water-entrainer-ethanol mixture is removed overhead via line 68, condensed in condenser 69 and collected in container 70 where it is phase separated. The upper entrainer phase is recycled via line 71 back to column 64 and the aqueous ethanol phase is recycled to column 25. Dry ethanol is removed as a bottom product from column 64 and stored in tank 75. The composition of the aqueous recycle to column 25 is given in Table 3b.

The composition of the entrainer recycle and dry ethanol from column 64 is given in Table 3d.

TABLE 3d

| Composition Components | Entrainer Recycle (Line 71) | Dry Ethanol (Line 74) |
|---|---|---|
| Entrainer | 721.12 | 0 |
| Ethanol | 105.26 | 216.6370 |
| Water | 8.02 | .0069 |
| Total | 834.40 | 216.6439 |

The dry ethanol from lines 74 and 76 is blended with 1,949.7261 lb. mole/hr. of gasoline from line 58 in line 54 to produce the gasohol blend shown in Table 3e.

TABLE 3e

| Composition Component | Final Gasohol Blend |
|---|---|
| Gasoline | 1,949.7261 |
| Ethanol | 216.6370 |
| Water | .0069 |
| Total | 2,166.3700 |

This gasohol blend contains less water than the blends of Examples 1 and 2 and can be used under any climatic conditions without encountering any difficulty due to phase separation of water. When operating according to this embodiment the ethanol content of the blend can be modified to any concentration by varying the amount of gasoline blended with it.

The scope of this invention is not limited to any particular gasoline to ethanol ratio since these components are miscible in all proportions. The current thinking is to blend sufficient ethanol to form a blend containing about 10 percent m ethanol. However, any blend containing both gasoline and ethanol at any proportions is within the scope of the invention which is to be limited only by the appended claims.

I claim:

1. A method of preparing a gasoline-ethanol blend suitable as a fuel for internal combustion engines comprising:
   (a) passing a feed consisting of a dilute aqueous ethanol solution to a distillation zone;
   (b) heating said dilute aqueous ethanol solution in said distillation zone and recovering, as a top product, concentrated aqueous ethanol containing about 45 to 89 percent m ethanol, and heated water as a bottom product;
(c) passing a gasoline feed to a heating zone where it is heated;
(d) introducing said concentrated aqueous ethanol and heated gasoline into a mixing zone to form a gasoline-ethanol-water mixture having a temperature of about 60° to 110° C.;
(e) passing said heated gasoline-ethanol-water mixture to a first separation zone wherein the mixture separates into a first upper gasoline-ethanol phase and a first lower aqueous phase containing some ethanol;
(f) passing said gasoline-ethanol phase through a cooling zone wherein the temperature is lowered to the minimum temperature under which the gasoline-ethanol is to be used as a fuel and into a second separation zone maintained at said minimum temperature wherein said mixture separates into a second upper gasoline-ethanol phase and a second lower aqueous phase; and
(g) withdrawing said second gasoline-ethanol phase from said second separation zone as a final gasoline-ethanol fuel blend.

2. A method according to claim 1 wherein the aqueous phases from the first and second separation zones are recycled to an extractive distillation zone along with the incoming dilute aqueous ethanol feed.

3. A method according to claim 2 wherein the gasoline entering the mixing zone has been heated in a heat exchanger by the heated water removed as a bottom product from the distillation zone.

4. A method according to claim 3 wherein a measured amount of gasoline is blended with a measured amount of the second gasoline-ethanol phase removed from the second separation zone to form a final gasoline-ethanol fuel blend.

5. A method according to claim 1 wherein the first lower aqueous phase is recycled to the dilute aqueous ethanol feed to the distillation zone, and the second lower aqueous phase is recycled to the gasoline feed prior to entering the heating zone.

6. A method of preparing a gasoline-ethanol blend suitable as a fuel for internal combustion engines comprising:
(a) passing a feed consisting of a dilute aqueous ethanol solution to a distillation zone;
(b) heating said dilute aqueous ethanol solution in said distillation zone and recovering from said zone a top product consisting of about 75 to 89 percent m ethanol, a side draw product consisting of about 45 to 80 percent m ethanol and heated water as a bottom product;
(c) passing said top product into an azeotropic distillation zone containing an entrainer selected from the group consisting of n-pentane and a heart cut gasoline and azeotropically distilling said product with said entrainer to remove overhead a mixture consisting of entrainer, ethanol and water and a bottom product of dry ethanol;
(d) allowing said mixture to phase separate into an entrainer phase and an aqueous ethanol phase and recycling the entrainer phase back to the azeotropic distillation zone and the aqueous phase back to the distillation zone;
(e) passing a gasoline feed to a heating zone where it is heated;
(f) introducing the side draw ethanol product from the distillation zone and heated gasoline into a mixing zone to form a gasoline-ethanol-water mixture having a temperature of about 60° to 110° C.;
(g) passing said heated gasoline-ethanol water mixture to a first separation zone wherein the mixture separates into a first upper gasoline-ethanol phase and a first lower aqueous phase containing some ethanol;
(h) passing said gasoline-ethanol phase through a cooling zone wherein the temperature is lowered to the minimum temperature under which the gasoline-ethanol is to be used as a fuel and into a second separation zone maintained at said minimum temperature wherein said mixture separates into a second upper gasoline-ethanol phase and a second lower aqueous phase, and
(i) withdrawing said second gasoline-ethanol phase from said second separation zone and blending a measured amount of said second gasoline-ethanol phase with a measured amount of dry ethanol from said azeotropic distillation zone to form a final gasoline-ethanol fuel blend.

7. A method according to claim 6 wherein a measured amount of gasoline is blended with a measured amount of dry ethanol from the azeotropic distillation zone and a measured amount of the second gasoline-ethanol phase removed from the second separation zone to form a final gasoline-ethanol fuel blend.

8. A method according to claim 7 wherein the aqueous phases from the first and second separation zones are recycled to an extractive distillation zone along with the incoming dilute aqueous ethanol feed.

9. A method according to claim 8 wherein the gasoline entering the mixing zone has been heated in a heat exchanger by the heated water removed as a bottom product from the distillation zone.

10. A method according to claim 6 wherein the first lower aqueous phase is recycled to the dilute aqueous ethanol feed to the distillation zone and the second lower aqueous phase is recycled to the gasoline feed prior to entering the heating zone.

* * * * *